United States Patent [19]

Fryer

[11] 4,186,749
[45] Feb. 5, 1980

[54] INDUCTION POWERED BIOLOGICAL RADIOSONDE

[75] Inventor: Thomas B. Fryer, Saratoga, Calif.

[73] Assignee: The United States of America as represented by the Administrator of the National Aeronautics and Space Administration, Washington, D.C.

[21] Appl. No.: 796,256

[22] Filed: May 12, 1977

[51] Int. Cl.² .............................................. A61B 5/00
[52] U.S. Cl. .................................. 128/748; 128/903; 73/724
[58] Field of Search ................ 128/2 P, 2.1 A, 2.05 E, 128/2.05 D, 2 R, 748, 903; 73/718, 724; 361/283

[56] References Cited

U.S. PATENT DOCUMENTS

| | | | |
|---|---|---|---|
| 3,422,324 | 1/1969 | Webb | 73/718 |
| 3,619,742 | 11/1971 | Rud | 73/724 |
| 3,757,770 | 9/1973 | Brayshaw et al. | 128/2.1 A X |
| 3,968,694 | 7/1976 | Clark | 73/724 |
| 4,026,276 | 4/1976 | Chubbuck | 128/2.05 E X |
| 4,062,351 | 12/1977 | Taylor et al. | 128/2 P X |

FOREIGN PATENT DOCUMENTS 1310439  3/1973  United Kingdom ............... 28/2 D

OTHER PUBLICATIONS

Pauley, J. et al. "An Implantable Multi-Channel Biotelemetry System", EEG and Clin. Neur. V 37 #2, Aug. 1974, pp. 153–160.
Collins, Carter C. "Miniature Passive Pressure Transensor for Implanting in the Eye", IEEE Transactions on Bio-Med Engineering vol. BME-14 #2 Apr. 1967.
Simard, J. M. et al. "Development of Telemetric Techniques for Use in Studies of the Electrical Activity of the Brain", ISA Transactions vol. 15 #3 pp. 246–252 1976.

*Primary Examiner*—Robert W. Michell
*Assistant Examiner*—Francis J. Jaworski
*Attorney, Agent, or Firm*—Darrell G. Brekke; John R. Manning; Armand McMillan

[57] ABSTRACT

An induction powered implanted monitor for epidurally measuring intracranial pressure and telemetering the pressure information to a remote readout. The monitor utilizes an L-C oscillator in which the C comprises a variable capacitance transducer, one electrode of which is a small stiff pressure responsive diaphragm. The oscillator is isolated from a transmitting tank circuit by a buffer circuit and all electric components in the implanted unit except an input and an output coil are shielded by a metal housing.

2 Claims, 7 Drawing Figures

INDUCTION POWERED BIOLOGICAL RADIOSONDE

ORIGIN

The invention described herein was made by an employee of the United States Government and may be manufactured and used by or for the Government for governmental purposes without the payment of any royalties thereon or therefor.

BACKGROUND OF THE INVENTION

1. Field of the Invention

Cerebral dysfunction in man is largely directly attributable to increased intracranial pressure. Whether this increase in pressure is precipitated by external injury (such as in the case of accident victims suffering significant head trauma) or internal injury (as in the case of victims of brain tumor, stroke, brain infection, or hydrocephalus) irreversible damage to the brain is caused by increasing intracranial pressure. Because there are both surgical and pharmacologic means of reducing intracranial pressure, a system which can accurately and continuously measure this important parameter with minimal risk and inconvenience to the patient is of significant clinical value.

The invention concerns itself with a minimally invasive biomedical system for continuously, chronically, and accurately monitoring intracranial pressure.

2. Description of the Prior Art

There is recognition in neurosurgical practice of the need to quantitatively measure and control intracranial pressure in ill patients. Several different types of transducers have been introduced for the measurement of intracranial pressure (ICP). Originally, "intracranial pressure" was defined as intraventricular fluid pressure. Over the last decade the definition has been broadened to encompass pressures measured at other locations within the cranium.

The dura mater, commonly called the dura, is a tough, fibrous membrane covering the brain and the spinal cord. Measurement of pressure within the brain has been accomplished by the insertion of cannulae into the lateral ventricles, but this is a difficult and dangerous task and not satisfactory for postoperative monitoring on the nursing ward. The position of the cannulae must be maintained with some precision, and because the dura has been breached, the risk of cerebral infection is markedly increased. The article "Radio Telemetry for the Measurement of Intracranial Pressure," James R. Atkinson et al., *Journal of Neurosurgery*, Vol. XXVII, No. 5, 1967, pages 428–432, discloses an ICP measuring system utilizing an implanted ventricular catheter with a resonant circuit. As the ICP varies, the resonant frequency of the resonant circuit changes. The frequency of the implanted resonant circuit is measured with a grid-dip circuit. The Atkinson device, in addition to offering a high risk of infection, utilizes a plastic container which has unwanted leakage, and an inductor (in the resonant circuit) which is susceptible to incontrollable variable extraneous capacity effects.

Early in this decade Majors, Schettini, Mahig and Nevis discovered that intracranial pressures could be measured with an epidurally implanted transducer (*Medical & Biological Engineering*, Vol. 10, 1972, pages 724–733). The accuracy of the measurement depends on the dura being in coplanar approximation with the sensing surface of the transducer. The papers of Yoneda et al. and Rudenberg et al. (*Surgical Neurology*, Vol. 1, January 1973, page 13; and 24th ACEMB, 1971, page 187, respectively) disclose the use of epidurally-placed pressure transducers. From the standpoint of patient acceptability they are completely unsatisfactory as they require wires to protrude from the scalp.

At the American Association of Neurological Surgeons, Americana Hotel, Bal Harbor, Fla., Apr. 6–10, 1975, messrs. Walker, Viernstein, Chubbuck and Karas described an "Intracranial Pressure Monitor" which comprises an L-C circuit in a cylindrical plastic container. The electrodes of the capacitor are each supported by a movable bellows. One side of the LEXAN ® case, the side placed next to the patient's dura, has a thin LEXAN ® diaphragm. The inductor and capacitor are engulfed in silicon oil. As the diaphragm is depressed, the bellows are compressed and the capacitance of the capacitor is increased. This results in a lowering of the resonant frequency of the parallel resonant circuit formed by the capacitor and inductor. The resonant frequency of the L-C circuit is monitored by an external detector that carries a frequency-modulated VHF signal that loses energy to the L-C circuit when the signal frequency passes through the resonant frequency of the L-C circuit.

The *Journal of Neurosurgery*, Vol. 44, April 1976, pages 465–478, contains an article by H. Grady Rylander et al. which describes an ICP monitoring system wherein an epidural pressure transducer with a variable inductance is part of the resonant circuit of a tunnel diode oscillator. The transducer comprises a coil with a movable ferrite core therein. The ferrite core is supported by a metal bellows one end of which is secured to the input diaphragm of the transducer. Power for the tunnel diode oscillator is inductively coupled from a power oscillator positioned close to the implanted transducer. A fixed capacitor is connected in parallel with the variable inductor to form a resonant circuit for the tunnel diode oscillator. An antenna coil is coupled in series with the L-C circuit to radiate an r-f signal to a remote receiver. The antenna coil is wound coaxially over the power coil and both coils are contained within a cylindrical Teflon ® housing. When the patient's dura moves the transducer diaphragm, the bellows flexes and varies the inductance of the coil. As the inductance changes, the frequency of oscillation of the tunnel diode oscillator changes. Tests conducted by the authors revealed a considerable discrepancy between epidural pressure and intraventricular fluid pressure a few days after the transducer was implanted.

The Walker and Rylander devices both suffer from similar shortcomings. In each device the resonant circuit is susceptible to extraneous distributed capacity effects which alter the resonant frequency and produces zero drift. LEXAN ® is known to creep and flow and it is not impervious to liquids. In the Walker device, creep in the LEXAN ® diaphragm causes zero drift. Fluids can penetrate the plastic housing of the Rylander monitor and alter the characteristics of the antenna coil. Inasmuch as the antenna coil is not buffered from the oscillator resonant circuit, extraneous distributed capacitance changes and mutual inductance effects in the antenna coil can produce unknown and undesirable deviations in the oscillation frequency of the tunnel diode oscillator. Antenna coil related pressure errors as large as 2 torr are acknowledged by Rylander. In order to achieve adequate inductance changes, the Rylander system must rely on large diaphragm motions. A soft bellows is accordingly dictated. When a soft bellows is utilized, sealing and hysteresis problems can be expected. Rylander indicates that his device has a hysteresis error as large as 0.7 torr. The Rylander and Walker transducers have very compliant diaphragms. The compliant transducers permit the dura to be distended and this results in inaccurate pressure measurements.

Therefore, there has been a recognized but unfulfilled need for an epidural intracranial pressure measuring system that may be used continuously and chronically and is free from hardwires and short-lived batteries and which is further characterized by minimal or no fluid leakage, hysteresis, and zero drift.

SUMMARY OF THE INVENTION

According to the present invention a very small electronic detector with a pressure transducer is implanted in a patient's head and secured to the cranium in such a manner that the pressure transducer touches the external side of the dura. The detector utilizes an L-C oscillator with a variable C that has a movable electrode in the form of a stiff pressure responsive digphragm. When the detector is implanted, the diaphragm touches the dura and senses the pressure thereof. Inasmuch as the diaphragm is stiff and has a very small full scale deflection, the arrangement between the dura and diaphragm is essentially coplanar and accurate pressure measurements result. No batteries are employed in the detector. Power for the unit is inductively obtained from a small battery-operated portable power oscillator that is placed near the top of the patient's head over the detector. The frequency of the L-C oscillator is directly proportional to the intracranial pressure measured by the pressure transducer. The oscillator signal is passed through a buffer circuit to a transmitting tank circuit comprising a coil with a shunt coupled capacitor. The buffer prevents the data transmitting coil from loading and detuning the oscillator. All components of the implanted detector except an input energy receiving coil and an output data transmitting coil are hermetically sealed within a noncorrosive metal housing that shields the L-C oscillator and buffer from extraneous distributed capacitance or mutual inductance effects that would alter the oscillator frequency and produce measurement errors.

The information coded signal from the data transmitting coil is inductively coupled to an r-f transmitting link which is housed with the power oscillator and stationed near the detector. The inductively coupled signal is converted to a signal in the audio band and that signal frequency modulates an r-f transmitter operating in one of the biomedical radio bands authorized by the FCC. A remote r-f receiver receives and demodulates the transmitted signal and feeds it to a readout which may be directly calibrated in intracranial pressure. Inasmuch as the detector is small, noncorrosive, free of batteries and connecting wires, it may be implanted in the skull and used as long as necessary to monitor intracranial pressure. The invention is characterized by very low zero drift and hysteresis.

DETAILED DESCRIPTION OF THE INVENTION

Figure 1:
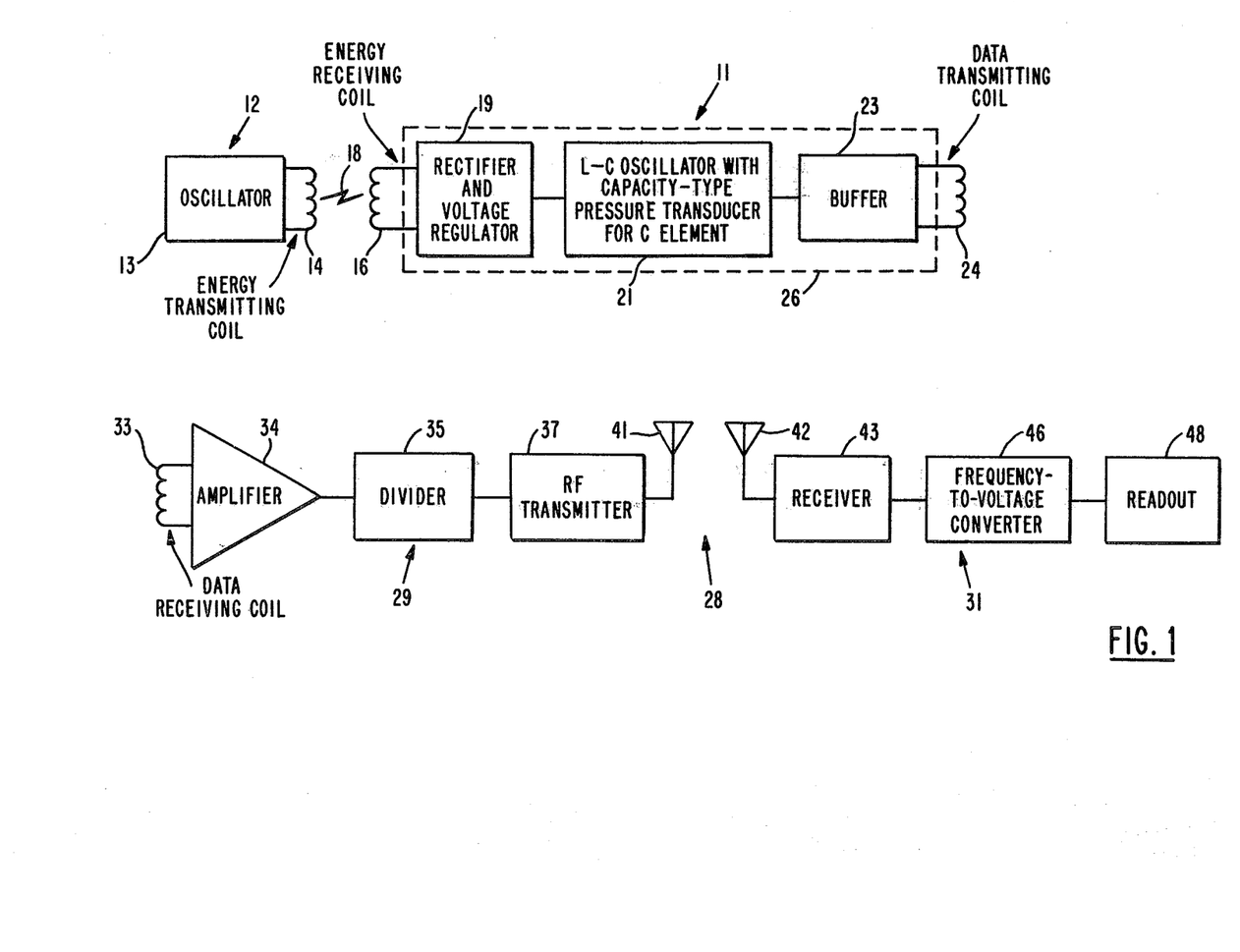
FIG. 1 is a block diagram generally illustrating the principal components of a biological radiosonde in accordance with the present invention.

Referring to FIG. 1, the implantable intracranial pressure detector 11 has no internal power supply such as a battery. Detector 11 receives its power inductively from energizer 12. Energizer 12 comprises a power oscillator 13 with a resonant L-C circuit wherein L is an energy transmitting coil 14. Factors such as power supply, coil geometry and distance between coils 14 and 16 is taken into account in selecting the oscillator frequency. Energizer 12 is preferably battery operated and contained in a small package which may be conveniently situated near the detector 11 whenever intracranial pressure is to be measured. The energy 18 inductively coupled from energy transmitting coil 14 to energy receiving coil 16 is rectified, filtered, and regulated in circuit 19. The single regulated d-c voltage supplied by circuit 19 is used to energize oscillator 21. Oscillator 21 has a parallel resonant L-C circuit with a capacitance-type pressure transducer and a fixed value inductor. The capacitance transducer has two eletrodes, a fixed one and an opposed movable one which takes the form of a pressure responsive diaphragm adapted to touch or couple to the dura of the patient. Oscillator 21 generates a signal the frequency of which is a direct function of the intracranial pressure measured by the capacitance-type pressure transducer incorporated in the resonant circuit. The signal is fed through buffer 23 to data transmitting coil 24. Circuits 19, 21 and 23 are contained within a metal housing 26 which shields oscillator 21 and keeps it immune from objects which could alter the distributed capacitance of the L-C resonant circuit and change the resonant frequency thereof. Buffer 23 has a very high input impedance and a low output impedance and effectively isolates coil 24 from oscillator 21 and prevents the coil from loading and detuning the oscillator. Coils 16 and 24 and circuits 19, 21 and 23 of detector 11 are all located under the scalp of the patient whose intracranial pressure is being monitored.

The energy radiated from coil 24 is converted to meaningful ICP information by processor 28 having an r-f transmitter link 29 and an r-f receiver link 31. Data receiving coil 33 is placed in proximity to data transmitting coil 24 and the energy radiated from coil 24 is inductively coupled to coil 33. The sine wave signal picked up by coil 33 is amplified in amplifier stage 34 and then passed through a frequency divider 35 to produce a signal in the audio band. The audio output signal of divider 35 is used to frequency modulate a conventional stable r-f transmitter 37 which operates in one of the biomedical radio bands approved by the FCC (for example, the transmitter could be operated in the 88–108 MHz or 174–215 MHz bands). Preferably, transmitter link 29 is made as small as possible with light weight materials, powered by a battery, and packaged in the same housing that contains energizer 12. One energizer/transmitting link constructed by the inventor used discrete electronic components and occupied approximately 50 cubic centimeters complete with the housing. The frequency modulated signal from r-f transmitter 37 is radiated by antenna 41 to receiving antenna 42 of a conventional FM receiver 43 which is tuned to the same frequency as the r-f transmitter 37. Whereas transmitter link 29 must be kept in proximity to the detector 11 implanted in the patient, receiving link 31 may be remotely located from the patient anywhere with the reception range of the signal transmitted by r-f transmitter 37. The demodulated signal at the output of receiver 43 bears the same frequency as the output signal from divider 35. The frequency of the signal emanating from receiver 43 is directly proportional to the intracranial pressure measured by detector 11. The output of receiver 43 is passed through a frequency-to-voltage converter 46 and the output signal of converter 46 is coupled to a readout 48. Readout 48 may, for example, comprise a meter calibrated in intracranial pressure and/or a recorder.

Inasmuch as the ICP information transmitted from detector 11 is coded as a function of signal frequency, the spacing and orientation of receiving coil 33 with respect to data transmitting coil 33 is not critical. All that is necessary is that coil 33 be close enough to coil 24 so that a detectable level of energy reach coil 33.

Figure 2:
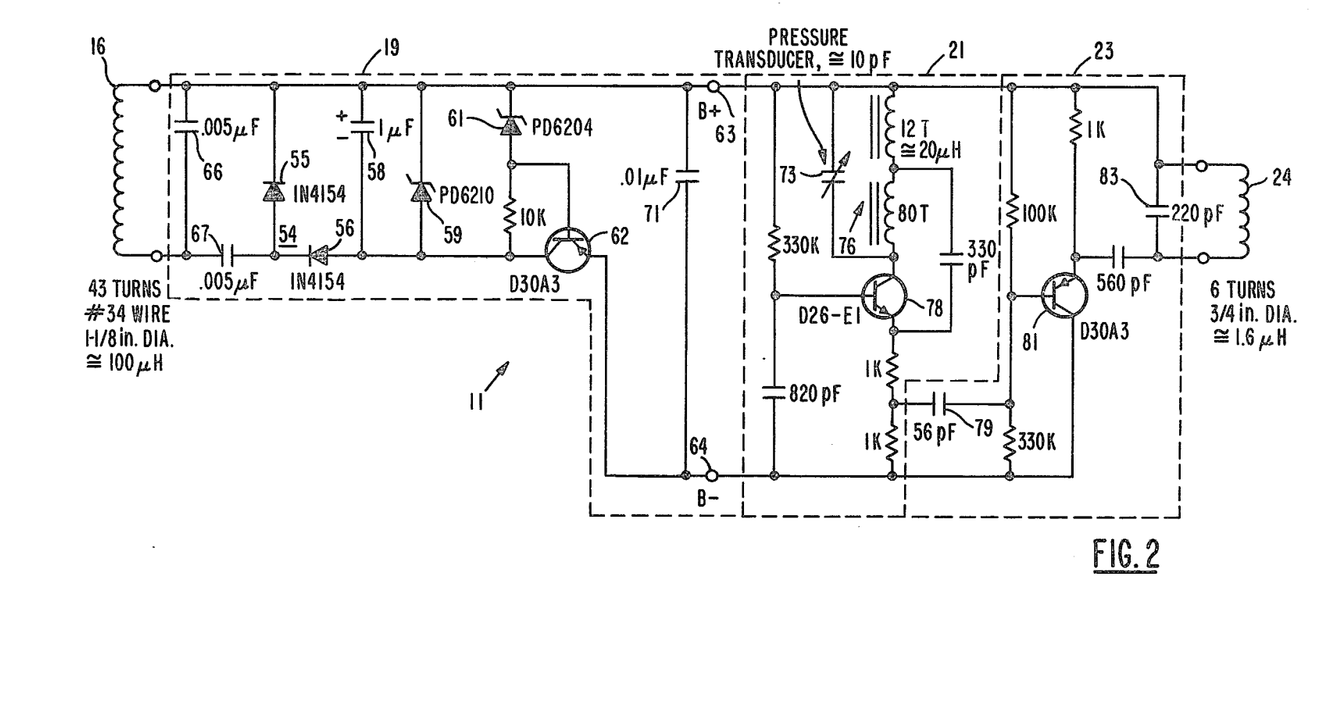
FIG. 2 is a schematic circuit diagram of the detector of FIG. 1.

FIG. 2 is a schematic diagram of the detector circuit. Capacitor 66 and energy receiving coil 16 form a resonant circuit tuned to the frequency of the energy emanating from coil 14. The sine wave signal inductively coupled to the resonant circuit is half-wave rectified in a cascade voltage doubling circuit 54 comprising diodes 55, 56 and capacitors 58, 67. Zener diodes 59, 61 and transistor 62 serve to regulate the d-c voltage at the output of the voltage doubler. The regulated d-c voltage across terminals 63 and 64 provides the necessary power for oscillator 21 and buffer 23.

Transistor 78 is configured as a Hartley oscillator with pressure transducer 73 and inductor 76 forming the parallel-coupled L-C tank circuit. Pressure cell 73 is a variable capacitor having a fixed electrode, and a movable electrode in the shape of a diaphragm. To measure intracranial pressure the diaphragm of the transducer is placed in contact with the dura of the patient that is to be monitored.

Transistor 81 is configured as an emitter follower. The output of oscillator 21 is coupled to the high impedance input of emitter follower by means of coupling capacitor 79. Data transmitting coil 24 is connected to the low impedance output of the follower. The rectifier/voltage-regulator 19, oscillator 21, and buffer 23 are contained within a metal housing that serves as an electrostatic shield (shown in FIG. 1 as 26) and prevents extraneous external distributed capacities and external fields from altering the frequency of the L-C oscillator 21. Buffer 23 isolates transmitting coil 24 from oscillator 21 and prevents external extraneous distributed capacities in the coil or mutual inductance effects from loading the oscillator and changing its frequency. Coil 24 is shunted by capacitor 83 in order to form an L-C resonant circuit having a resonant frequency on or near the center of the band swept by the oscillator as the diaphragm of transducer 73 encounters different pressures.

Figure 3:
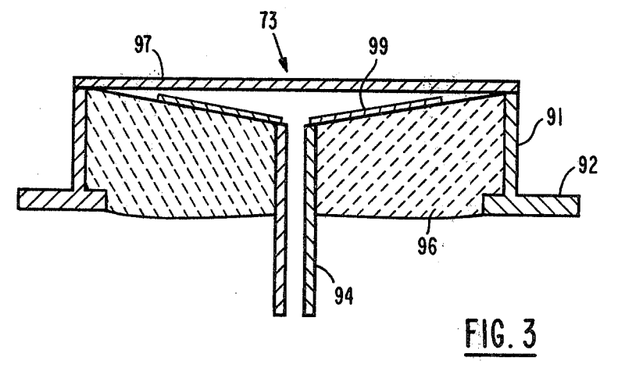
FIG. 3 is a cross-sectional view of the pressure transducer used in the detector.

FIG. 3 depicts a cross-sectional view of the pressure transducer 73. The transducer has a generally tubular shell or body 91 composed of a metallic material. Body 91 has a radial extension 92 which permits the transducer to be secured and sealed to the housing for rectifier/voltage-regulator 19, oscillator 11, and buffer 23. An electrically conductive tube 94, also preferably of metal, is centrally positioned within body 91 so as to be coaxial therewith. Filling the space between the outer surface of tube 94 and the inner surface of body 91 is a solid insulating substance 96, such as glass or ceramic which is hermetically sealed to members 91, 92 and 94. Kovar ® has, for example, been found to be a suitable material for insulator 96. The upper surface of insulating substance 96 is provided with a metallic film 99, preferably produced by painting the insulation with gold chloride and then firing the assembly. The conductive film 99 contacts, and may overlie, the end of tube 94, but is not in electrical engagement with diaphragm 97 or body 91. A pressure responsive diaphragm 97, formed of a metallic material having essentially the same coefficient of linear expansion as that of body 91, is placed in tension and welded around the rim of body 91.

If the diaphragm is large and compliant, the dura thereunder can appreciably distend and cause false pressure measurements. It is important, therefore, that the diaphragm be stiff. In a diaphragm, the stiffness can be characterized as the pressure required to produce unit deflection. The elastic modulus of the diaphragm material, the diaphragm diameter and thickness, and the diaphragm tension must be chosen so as to make the diaphragm stiff. That is, for a full scale reading, the diaphragm deflection should be small. In a preferred form of construction the diaphragm diameter was 7 mm, the thickness was 0.012 mm, and the full scale deflection (representing 50 torr) was 0.005 mm (0.0002 inches) for a stiffness of $$\frac{50 \text{ torr}}{.005 \text{ mm}} = \frac{50 \text{ torr}}{5 \text{ micron}} = \frac{10 \text{ torr}}{\text{micron}}$$

Figure 4:
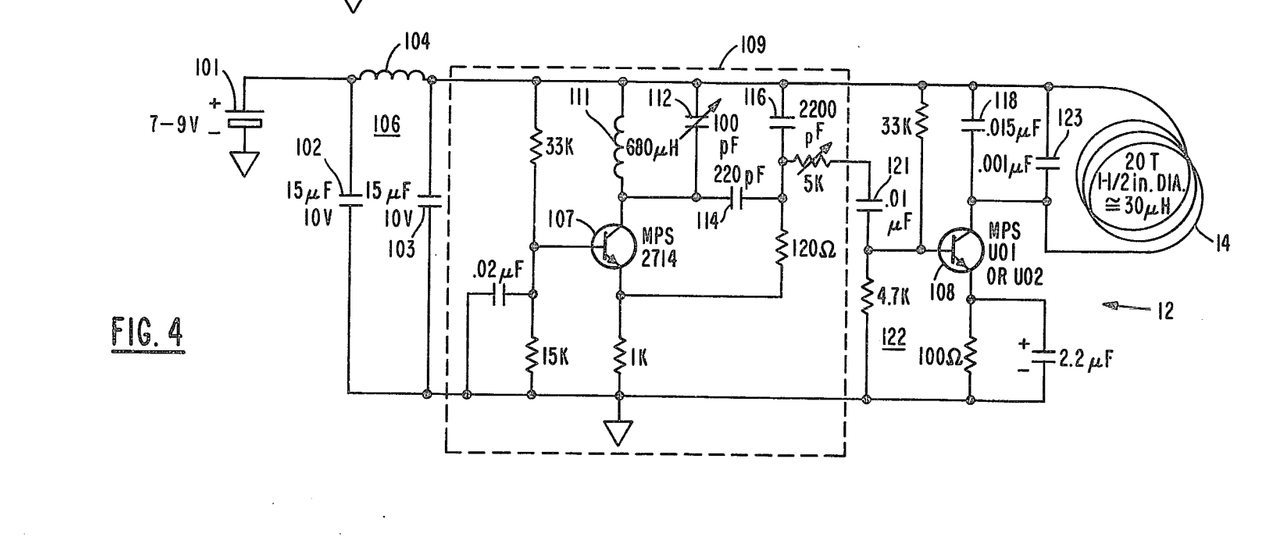
FIG. 4 is a schematic circuit diagram of the energizer of FIG. 1.

A schematic diagram of the energizer 12 is depicted in FIG. 4. A transistor 107 is configured as a Colpitts-type oscillator 109 with a tank circuit comprising inductor 111 and capacitors 112, 114 and 116. The frequency of the oscillator is not critical and may vary from the audio range to over a MHz. In one construction form, using the component values shown in FIG. 4, oscillator 109 oscillated at a frequency of approximately 240 KHz. The output of oscillator 109 is coupled to a power amplifier 122 by means of coupling capacitor 121. The collector of amplifier transistor 108 is connected to a tank circuit comprising energy transmitting coil 14 and capacitors 118 and 123. The values of capacitors 118 and 123 are selected so that the tank circuit will resonant at the same frequency as the oscillator (240 KHz). The power for oscillator 109 and amplifier 122 is supplied by a small battery 101. In operation, the energizer 12 is placed so that the energy transmitting coil 14 is in proximity to energy receiving coil 16 of detector 11. In one construction form (utilizing components with the values shown in FIGS. 2 and 4), the energy from energizer 12 generated an oscillator and buffer supply voltage of 4.5 volts in detector 11.

Figure 5:
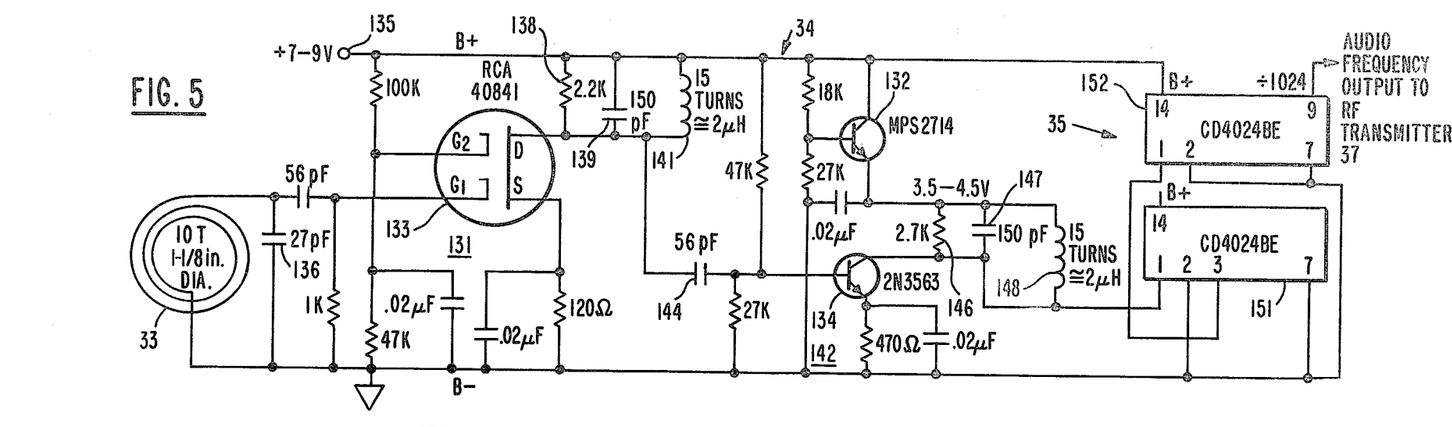
FIG. 5 is a schematic circuit diagram of the data receiving coil, amplifier, and divider of the r-f transmitter link.

FIG. 5 discloses the schematic circuit diagram for data receiving coil 33, amplifier 34 and divider 35 of r-f transmitter link 29. Amplifier 34 comprises two stages of amplification built around MOS FET 133 and NPN transistor 134, respectively. Amplifier 131 has an input tank circuit comprising data receiving coil 33 and shunt-connected capacitor 136, and an output tank circuit comprising parallel-connected capacitor 139, inductor 141 and resistor 138. Resistor 138 lowers the Q of the circuit and broadens the passband so that the amplifier will pass all frequencies generated by oscillators 21 in detector 11. The oscillation frequency of oscillator 21 is not critical. In one construction form, using the values depicted in FIGS. 2 and 5, oscillator 21 had a base frequency of 8 MHz at zero torr intracranial pressure and a frequency of 8.3 MHz at full scale transducer deflection (50 torr), and amplifier 34 had a passband from 7–10 MHz. The output of amplifier 131 is coupled to amplifier 142 by means of coupling capacitor 144. The collector of transistor 134 is connected to shunt-connected inductor 148, capacitor 147 and resistor 146. The tank circuit is tuned to the same passband as amplifier 131 (7–10 MHz). The output of amplifier 142 is connected to a divider 35 comprising series-connected binary counters 151 and 152. The divider is employed to reduce the frequency of the inductively coupled input signal down to a frequency within the audio band. If the signal modulating r-f transmitter 37 is too high, the bandwidth of the signal from r-f transmitter 37 will exceed the limits permitted by the FCC. Three binary stages are employed in counter 151 and it divides by $2^3$, whereas all seven stages of counter 152 are used and it divides by $2^7$. Thus, the frequency of the signal inputed to counter 151 is divided by 1024 ($2^{10}$) before it leaves counter 152. For example, if a signal having a frequency of 8.1 MHz were inductively coupled into amplifier 34 from detector 11, the signal would be divided down to a signal having an audio frequency of 7,910.16 Hz. The output of divider 35 is coupled to r-f transmitter 37 and the audio frequency is used to frequency modulate the r-f carrier. Alternatively, the output of divider 35 may be fed directly to a frequency counter that is calibrated in terms of intracranial pressure. As stated before, r-f transmitter link 29 (FIG. 1) and energizer 12 are preferably packaged in the same container. In order to reduce the volume of the container, one battery 101 (FIG. 4) is employed for both circuits. Inductor 104 and capacitors 102, 103 form a pi filter to block the 240 MHz signal from reaching the B+ input terminal 135 of r-f transmitting link 29 (FIG. 5). If a separate battery is used for link 29, pi filter 106 may be eliminated. Transistor 132 reduces the supply voltage for amplifier 142 so that the amplifier output signal will not exceed the voltage limit of the divider.

Figure 6:
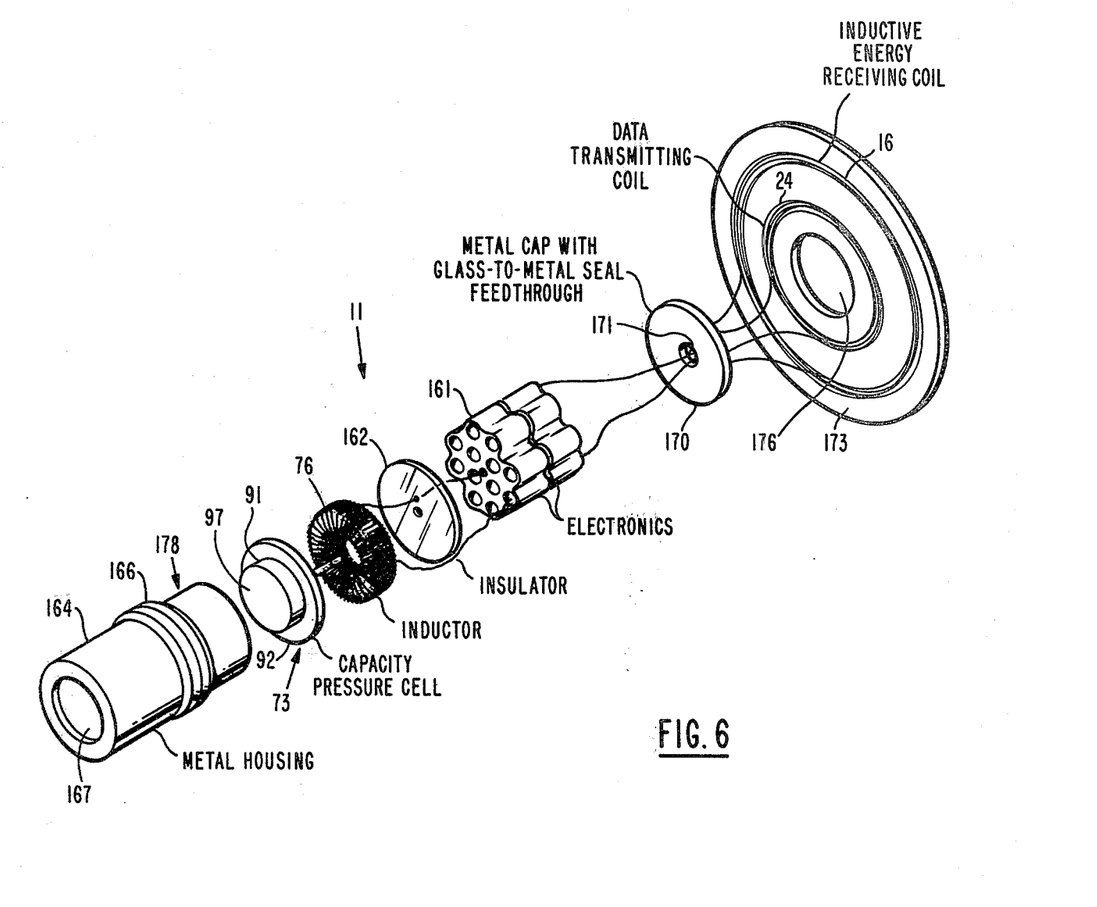
FIG. 6 is an exploded perspective view of the detector of FIG. 1.

FIG. 6 depicts an exploded perspective view of a preferred packaging arrangement for the detector 11. All of the circuit components of detector 11 except energy receiving coil 16, data transmitting coil 24, pressure transducer 73, and inductor 76 are potted in a conglomerate 161. An insulator disc 162 isolates the inductor 76 from conglomerate 161. Diaphragm 97 of transducer 73 protrudes from a circular opening 167 in one end of a generally cylindrical metal housing 164 having external coarse threads 166. The radial extension 92 of transducer 73 is hermetically sealed to the inner end surface of housing 164 by welding or some other suitable process. A metal cap 170 is hermetically sealed to the other end of housing 164. A glass-to-metal seal 171 with two lead feedthroughs is centrally positioned in cap 170. Energy receiving coil 16 and data transmitting coil 24 are coaxially arranged and imbedded in a plastic disc 173 with a centrally located aperture 176. Disc 173 encircles end 178 of housing 164 and is secured thereto with a non-toxic adhesive (not shown). One end of coil 16 and one end of coil 24 are electrically connected to metal cap 170 (B+). The other ends of these coils are connected to the two lead feedthroughs in glass-to-metal seal 171, respectively. The short coil ends running from disc 173 to the housing are secured and sealed from moisture by an inert electrically insulative adhesive substance such as epoxy. Further, the glass-to-metal seal is covered with a coating of epoxy to insure that seal 171 does not corrode. It is clear from FIG. 6 that housing 164 and cap 170 form an electrostatic shield for all components of the detector other than coils 16 and 24. Detector 11 would be inoperative if the coils were shielded. The metal material that has been found to be entirely free from corrosion while implanted in a subject is titanium. Therefore, the preferred material for transducer body 91, diaphragm 97, housing 164 and cap 170 is titanium. The inventor has utilized stainless steel and gold-plated brass for the above-mentioned items; however, he has not found these metals to be as satisfactory as titanium.

Figure 7:
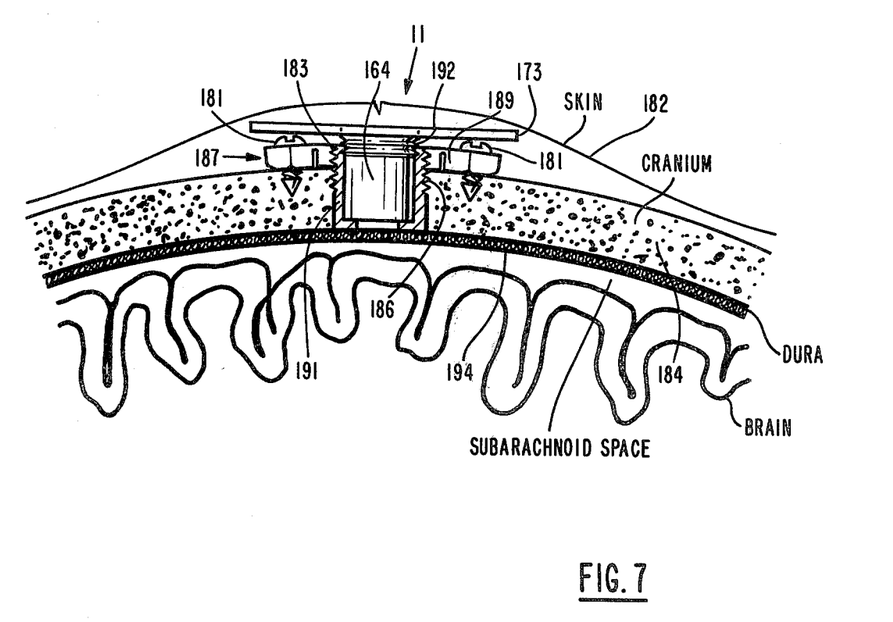
FIG. 7 is a cross-sectional view depicting the detector implanted in a patient's head.

The detector 11 may be implanted in the patient's head through an incision in the skin 182 (FIG. 7). A standard air-driven trephine or brace trephine may be used to make the hole in the cranium 184. Bleeding may be controlled by bone wax and electrocautery. After the hole is made, a collar 187 with arms 189 is secured to the skull by means of self-threading screws 181. Centrally located in collar 187 is an aperture with threads 183. A generally cylindrical sleeve 191 has internal threads 192 and external threads 183. Detector 11 is screwed into sleeve 191 until housing 164 reaches the inner end surface of the sleeve. The sleeve thickness is chosen so that the outer surface of diaphragm 97 is flush with the outer end surface of sleeve 191. Then the sleeve with the mated detector 11 is screwed into collar 187 until diaphragm 97 touches dura 194. The galea of the scalp is then sutured. A dressing may be applied or the wound may be sealed with a plastic spray. A dressing will not interfere with signals reaching coil 16 or leaving coil 24.

It is preferable that screws 181, collar 189 and sleeve 191 be made from an inert plastic material such as Teflon ®. Inasmuch as detector 11 has no batteries to wear out, it may be left in the patient's head for as long as the neurosurgeon desires to monitor intracranial pressure. As soon as the energizer 12 is turned on and placed near detector 11, detector 11 is activated and transmits a signal having a frequency which is a direct function of the intracranial pressure. The signal is inductively coupled to data receiving coil 33 (which is housed in the same package as energizer 12), the frequency of the signal is converted to a frequency in the audio band and the audio signal frequency modulates a stable r-f transmitter (preferably one which is crystal controlled). Operating within the power limits dictated by the FCC, such a telemeter typically has a range of 100 to 200 feet. FM receiver 43 detects the r-f energy transmmitted by transmitter 37 and converter 46 produces an analog voltage which is representative of the intracranial pressure. Readout 48 may be a meter calibrated in terms of intracranial pressure or it may be a magnetic or pen-type recorder.

Five intracranial pressure monitors made in accordance with the subject invention were pressure cycled in a water bath environment by the Biomedical Application Team of the Stanford University School of Medicine for a period of 50 days. The monitors were found to have a zero drift of less than 0.1 torr/day and a hysteresis error less than 0.1 torr. The maximum error produced by external extraneous distributed capacities was under 0.1 torr.

Although the above description has been directed to system for measuring intracranial pressure, it is to be understood that detector 11 could be implanted in other parts of a patient to measure other internal pressures.

What is claimed is:

1. A detector for measuring intracranial pressure at a subject's dura and adapted to function in proximity to a source of electromagnetic energy, said detector comprising:

an oscillator with an L-C resonant circuit, said C of said resonant circuit comprising a capacitance-type pressure transducer, said transducer having a first electrode comprising a pressure-responsive diaphragm and a second fixed electrode opposite said first electrode, said diaphragm being a stiff metal disc hermetically sealed to one end of a metal tubular body, said diaphragm having a stiffness at least as great as 10 torr per micron, the frequency of said oscillator being the direct function of the intracranial pressure sensed by said diaphragm when said diaphragm contacts said subject's dura;

a second resonant circuit having a data transmitting coil and a capacitor;

a buffer having an input with a high impedance and an output with a low impedance, said oscillator being coupled to said buffer input and said data transmitting coil being coupled to said buffer output;

a cylindrically-shaped metal housing having a band of threads on the outer surface thereof said housing having a diameter larger than said transducer, said transducer being sealed to one end of said housing with said diaphragm and part of said tubular body projecting outside of said housing, the housing surrounding said transducer forming a shoulder, said diaphragm being a distance X from said shoulder, means for sealing the other end of said housing, said oscillator, said capacitor of said second resonant circuit, said buffer and said converting means all being hermetically sealed within said metal housing;

a collar with internal threads;

means for fastening said collar to a patient's cranium;

a sleeve with external and internal threads, said external threads adapted to mate with said collar threads, said internal threads adapted to mate with said housing threads, said sleeve having an end plate with an inner and an outer surface and a centrally located aperture slightly larger than said diaphragm, said aperture permitting a user to see when said sleeve has been advanced in said collar to the position where the end plate outer surface is flush with said subject's dura, said end plate being X thick so that said transducer diaphragm will be flush to said outer surface of said sleeve and plate when said housing is screwed all the way into said sleeve and said shoulder touches said inner surface.

2. A detector for measuring intracranial pressure and adapted to function in proximity to an energizer radiating electromagnetic energy, said detector comprising:

an oscillator with an L-C circuit, said C of said tank circuit comprising a variable capacitor having a fixed electrode and a movable electrode that is a stiff pressure-responsive diaphragm, the frequency of said oscillator being representative of the pressure sensed by said diaphragm;

a second resonant circuit having a data transmitting coil and a parallel-coupled capacitor;

a buffer having an input with a high impedance and an output with a low impedance, said oscillator being coupled to said buffer input and said second resonant circuit being coupled to said buffer output;

an energy receiving coil for receiving said electromagnetic energy;

means coupled to said energy receiving coil for converting said electromagnetic energy to a regulated supply voltage for said oscillator and said buffer;

a cylindrically-shaped metal housing having first and second ends disposed on the longitudinal axis of said housing, said transducer being sealed to said first end with said diaphragm normal to said axis and displaced outwardly from said housing;

said oscillator, said parallel-coupled capacitor, said buffer, and said energy converting means being sealed within said metal housing, a glass-to-metal seal situated in said second housing end;

a plastic disc fastened to said second housing end and disposed normal to said housing axis, said coils being concentrically arranged and imbedded in said disc, the ends of said data transmitting coil passing through said glass-to-metal seal to said parallel-coupled capacitor, and the ends of said energy receiving coil passing through said glass-to-metal seal to said energy converting means; and means for supporting said metal housing on a patient's cranium, said supporting means enabling said transducer diaphragm to be coplanar with the patient's dura.

* * * * *